United States Patent [19]
Lauilhé et al.

[11] Patent Number: 6,010,978
[45] Date of Patent: Jan. 4, 2000

[54] HERBICIDAL COMPOSITIONS CONTAINING TERPENE HYDROCARBONS

[75] Inventors: Jean-Paul Lauilhé, Saint Paul Les Dax; Chislain Dufau, Dax, both of France

[73] Assignee: Action Pin, Dax, France

[21] Appl. No.: 08/666,291

[22] PCT Filed: Dec. 26, 1994

[86] PCT No.: PCT/FR94/01533

§ 371 Date: Aug. 19, 1996

§ 102(e) Date: Aug. 19, 1996

[87] PCT Pub. No.: WO95/17822

PCT Pub. Date: Jul. 6, 1995

[30] Foreign Application Priority Data

Dec. 24, 1993 [FR] France ................................. 93 15653

[51] Int. Cl.$^7$ ..................................... A01N 25/30
[52] U.S. Cl. .................. 504/116; 504/270; 504/301; 504/304; 504/309; 504/319
[58] Field of Search ................... 504/116, 309, 504/270, 319, 304, 301; 71/DIG. 1

[56] References Cited

U.S. PATENT DOCUMENTS

| | | | |
|---|---|---|---|
| 3,776,714 | 12/1973 | Bordenca | 71/98 |
| 3,871,863 | 3/1975 | Dorschner et al. | 71/88 |
| 4,822,407 | 4/1989 | Esposito | 71/94 |

FOREIGN PATENT DOCUMENTS

| | | |
|---|---|---|
| 0 022 666 | 1/1981 | European Pat. Off. . |
| 0 027 344 | 4/1981 | European Pat. Off. . |
| 2 134 391 | 8/1984 | United Kingdom . |
| 80/02360 | 11/1980 | WIPO . |
| 91/05472 | 5/1991 | WIPO . |
| 93/19598 | 10/1993 | WIPO . |

OTHER PUBLICATIONS

H. Martin, "The Scientific Principles of Plant Protection", E. Arnold. London GB, pp. 75–81, 1994.
C. Gauvrit et al., "Oils for Weed Control: Uses and Mode of Action", Pestic. Sci., vol. 37, pp. 147–153, 1993.
ACS abstract, AN 122:25843, "Possibility of Reducing Dosage of Pesticides in Potato Protection", Kowanski et al. Mater, Ses. Navk. Inst., 1992, 31(2) 66–70.
ACS abstract, AN 116:78605 corresponding to JP 03086802 A2 published 910411 Heisei, 1991.
ACS abstract, AN 119:65585, "Volatile monoterpenes as potential parent structures for new herbicides", Vaughn et al., Weed Sci., (1993), 41(1) 114–119.
Derwent abstract, WPI, AN:94–310851, corresponding to AU 5194293D, 1994.

Primary Examiner—S. Mark Clardy
Attorney, Agent, or Firm—Wenderoth, Lind & Ponack, L.L.P.

[57] ABSTRACT

The present invention relates to the use of at least one terpenic carbide and/or a derivative thereof as additive to a culture selective herbicide slurry or as a coformulant in a culture selective herbicide composition, intended to be applied between spearing and blossoming of the culture(s).

23 Claims, No Drawings

HERBICIDAL COMPOSITIONS CONTAINING TERPENE HYDROCARBONS

BACKGROUND OF THE INVENTION

1. Field of the Invention

The invention relates to the use of a formulation based on at least one terpene hydrocarbon and/or one of its derivatives, in particular pine oil, and optionally on a surface-active agent, as adjuvant of a selective herbicidal composition or mixture.

2. Description of Related Art

Farmers use, on the different species which they grow, herbicides which are selective for the crop, in order to destroy the weeds while leaving the crop unharmed. These selective herbicides are used early, for example between emergence and stem elongation (at the latest coming into ear or flowering) of annual crops, in order to decrease the impact of competition from weeds on the yield. Under these conditions, they must be completely selective. These products have a foliar or root effect or both simultaneously.

The foliar effectiveness of these products can be improved by the use of adjuvants; this practice often has the effect of decreasing the selectivity of the mixture.

SUMMARY OF THE INVENTION

It has been discovered that the use of at least one terpene hydrocarbon and/or one of its derivatives according to the invention increases, in significant proportions, the effectiveness of the herbicides while retaining excellent selectivity of the mix with respect to the crop; moreover, the consistency of effect of the herbicide is also improved.

The subject of the invention is the use of at least one terpene hydrocarbon and/or one of its derivatives as adjuvant of a selective herbicidal mixture for cultivated areas or as coformulant of a selective herbicidal composition for cultivated areas, for the treatment of crops between emergence and coming into ear or flowering.

As coformulant, the terpene hydrocarbons and/or their derivatives may be intended, for example, for a manufacturer who will incorporate them as coformulant during the manufacture of the said herbicidal composition, at the same time as the active material and the different normal ingredients of such a composition. They may be intended for a final user, for example for a farmer, in which case it will preferably be formulated in combination with a compatible surface-active agent, in order to form an adjuvant. This adjuvant will be intended to be added to a dilute herbicidal mixture.

Advantageously, in the case where the terpene hydrocarbons and/or their derivatives are formulated in conjunction with a surfactant, the formulation will comprise from 95 to 60% by weight of terpene hydrocarbon or derivative of the latter and from 5 to 40% by weight of a surface-active agent, preferably 20 to 30% by weight of surface-active agent.

DETAILED DESCRIPTION OF THE PREFERRED EMBODIMENT(S)

The terpene derivatives within the meaning of the present invention are of all types of terpene hydrocarbon having 2, 3 or 2n isoprene units per molecule, with n ranging from 2 to 8 and even beyond. They are mono-, sesqui-, di-, tri-, tetra- and polyterpenes.

The terpene hydrocarbons can be acyclic, monocyclic or bicyclic.

Mention may in particular be made of the following examples:

acyclic terpene hydrocarbons: myrcene, alloocimene, and the like monocyclic terpene hydrocarbons: dipentene, terpinolene, p-cymene, and the like bicyclic terpene hydrocarbons: $\alpha$-pinene, $\beta$-pinene, $\Delta$-3-carene and the like.

Terpene hydrocarbon derivatives are understood to mean in particular the following compounds:

a—oxidized derivatives: cineols b—terpene alcohols: borneol, fenchol, menthanol, terpineols, and the like c—ketones: camphor, fenchone d—terpene resins derived, for example, from $\alpha$-pinene and $\beta$-pinene e—terpene phenolic resins, and the like f—esters: terpenyl acetate, and the like.

The invention also comprises mixtures of terpene alcohols and hydrocarbons, for example pine oil of natural or synthetic origin (obtained, for example, by catalytic hydration of $\alpha$-pinene).

Pine oils are composed of mixtures of terpene hydrocarbons and alcohols which can contain from 50% by weight of terpene alcohols, preferably 80 to 90% by weight.

The surface-active agent comprises any agent capable of emulsifying the terpene hydrocarbon and/or a derivative of the latter when it is added to the herbicidal mixture.

In particular, the surface-active agent can comprise an anionic surface-active agent, for example an alkali metal alkyl sulphate, in particular a sodium alkyl sulphate, for example a product marketed under the name MELIORAN 118® by the company CECA, a non-ionic surface-active agent, such as an ethoxylated alkylphenol, a cationic surface-active agent or alternatively a mixture of one or a number of these agents, in particular a mixture of one or a number of cationic surface-active agent(s) and of one or a number of non-ionic surface-active agent(s) or of one or a number of anionic surface-active agent(s) and of one or a number of non-ionic surface-active agent(s).

The nature of the herbicidal agent is material.

The invention relates to all selective herbicides for crops, in particular those with a significant foliar effect, whatever the crop concerned (cereals, peas, rape, sunflower, maize, beet, potato or others). The use is especially advantageous in combination with herbicides for grass control in cereals or alternatively with herbicides for the control of broad-leaved weeds in dicotyledon crops. Mention may be made, among the families of herbicidal agents, of aryloxyphenoxypropionates, phenoxynicotinanilides, benzonitriles, carbamates, benzofuran derivatives and pyridyl phenyl ethers.

The herbicidal agents which have furnished particularly advantageous results are:

fenoxaprop-p-ethyl;

diflufenican, ioxynil, bromoxynil and mixtures thereof;

phenmedipham, ethofumesate and mixtures thereof;

clodinafop-propargyl+chloquintocetmexyl (CELID®, Ciba-Geigy).

Advantageously, the adjuvant formulation described above is used in the proportion of 0.25 liter to 1 liter per 100 liters of herbicidal mixture, corresponding to doses of 0.25 to 4 liters/hectare, the doses of herbicidal mixtures generally being from 100 to 400 liters/hectare.

A surprising activity has been observed when at least one terpene hydrocarbon and/or one of its derivatives and optionally one surface-active agent are added extemporaneously to the herbicidal mixture before use.

One formulation example is based on pine oil and on a surface-active agent and is the product sold by Dérivés Résiniques et Terpéniques under the name HELIOSOL®.

Another subject of the invention is a herbicidal composition comprising a herbicidal agent in combination with the usual ingredients of herbicidal compositions and at least one terpene hydrocarbon and/or one of its derivatives, in particular pine oil, as coformulant.

The said herbicidal composition usually comprises a herbicidal agent in combination with the usual ingredients of herbicidal compositions and a formulation comprising from 95 to 60% by weight of at least one terpene hydrocarbon and/or one of its derivatives and from 5 to 40% by weight of a surface-active agent.

In this case, the gain in effectiveness due to the addition of the coformulant makes it possible to reduce the effective dose of active material in a proportion which can reach 50%.

Another subject of the invention is a ready mix dilute herbicidal composition comprising, per 100 liters of herbicidal mixture, from 0.25 to 1 liter of a formulation comprising from 95 to 60% by weight of at least one terpene hydrocarbon and/or one of its derivatives, preferably a pine oil and from 5 to 40% by weight of a surface-active agent and a herbicidal agent present in an amount of between the usual doses and 50% of the usual dose.

The results obtained by using HELIOSOL® as adjuvant of different herbicidal mixtures will be given below.

The decrease in the coefficients of variation is the proof of the consistency of effect observed on using the formulation according to the invention as adjuvant of a herbicidal mixture.

EXAMPLE 1

Combination of HELIOSOL® with fenoxaprop-p-ethyl. Post-emergence weed control in wheat. Volume of mixture 200 l/ha. Tests on grasses: foxtails and/or wild oat (France 1993, Vienne).

|  | Fenoxaprop-p-ethyl (g/ha) | HELIOSOL® (l/ha) | Effectiveness (%) | Coefficient of variation |
|---|---|---|---|---|
| TEST 1 | 82.8 | / | 95.0 | 9.1 |
| TEST 2 | 82.8 | 0.5 | 97.3 | 6.3 |
| TEST 3 | 82.8 | 1 | 100.0 | 1.7 |
| TEST 4 | 55.2 | 1 | 99.1 | 2.2 |
| TEST 5 | 41.4 | 1 | 98.8 | 2.8 |

EXAMPLE 2

Same combination as that described above. Post-emergence weed control in wheat. Volume of mixture: 230 l/ha. Tests on grasses (France 1993, Somme).

|  | Fenoxaprop-p-ethyl (g/ha) | HELIOSOL® (l/ha) | Effectiveness (%) |
|---|---|---|---|
| TEST 1 | 82.8 | / | 99.3 |
| TEST 2 | 82.8 | 1.17 | 100.0 |
| TEST 3 | 55.2 | 1.17 | 99.8 |

EXAMPLE 3

Combination of HELIOSOL® with a speciality product containing a mixture of diflufenican (40 g/l)+ioxynil (75 g/l)+bromoxynil (125 g/l). Post-emergence weed control in wheat. Volume of mixture: 200 l/ha. Tests on dicotyledons (France 1993, Vienne).

| A. Test on pansies | | | | | |
|---|---|---|---|---|---|
|  | Diflufenican g/ha | Ioxynil g/ha | Bromoxynil g/ha | HELIOSOL® l/ha | Effectiveness (%) | Coefficient of variation |
| TEST 1 | 80 | 150 | 250 | / | 85 | 21 |
| TEST 2 | 80 | 150 | 250 | 1 | 100 | 0 |
| TEST 3 | 80 | 150 | 250 | 2 | 100 | 0 |
| TEST 4 | 60 | 112.5 | 187.5 | 1 | 100 | 0 |
| TEST 5 | 40 | 75 | 125 | 1 | 89 | 13 |

| B. Tests on poppies | | | | | |
|---|---|---|---|---|---|
|  | Diflufenican g/ha | Ioxynil g/ha | Bromoxynil g/ha | HELIOSOL® l/ha | Effectiveness (%) | Coefficient of variation |
| TEST 1 | 80 | 150 | 250 | / | 21 | 176 |
| TEST 2 | 80 | 150 | 250 | 0.5 | 100 | 0 |
| TEST 3 | 80 | 150 | 250 | 1 | 100 | 0 |
| TEST 4 | 80 | 150 | 250 | 2 | 100 | 0 |
| TEST 5 | 60 | 112.5 | 187.5 | 1 | 100 | 0 |
| TEST 6 | 40 | 75 | 125 | 1 | 49 | 28 |

| C. Tests on speedwells (ivy-leafed) | | | | | |
|---|---|---|---|---|---|
|  | Diflufenican g/ha | Ioxynil g/ha | Bromoxynil g/ha | HELIOSOL® l/ha | Effectiveness (%) | Coefficient of variation |
| TEST 1 | 80 | 150 | 250 | / | 41 | 105 |
| TEST 2 | 80 | 150 | 250 | 1 | 58 | 74 |
| TEST 3 | 80 | 150 | 250 | 2 | 100 | 0 |
| TEST 4 | 60 | 112.5 | 187.5 | 1 | 63 | 41 |
| TEST 5 | 40 | 75 | 125 | 1 | 50 | 100 |

In the 3 examples above, it was possible to confirm the advantage of combining 1 l/ha (0.5 l/hl) of HELIOSOL® with reduced doses of herbicides. In all the cases, HELIOSOL® appears as being selective in wheat cultivation.

EXAMPLE 4

Combination of HELIOSOL® with a speciality product containing a mixture of phenmedipham (97 g/l)+ethofumesate (94 g/l). Post-emergence weed control in sugar beet. Volume of mixture 300 l/ha (France 1990, Marne).

|  | TEST 1 | TEST 2 |
|---|---|---|
| Phenmedipham (l/ha) | 485 | 485 |
| Ethofumesate (l/ha) | 470 | 470 |
| HELIOSOL® (l/ha) | / | 1 |
| Effectivenesses (E1/E2)* (%/%) | | |
| Scarlet pimpernel | 91.67/89.66 | 100/100 |
| Fat hen | 88.89/87.5 | 99.44/87.5 |
| Common chickweed | 73.33/85.71 | 86.67/100 |
| Field bindweed | 60.69/40.63 | 95.38/93.75 |

-continued

|  | TEST 1 | TEST 2 |
|---|---|---|

*E1: Effectiveness 2 to 3 weeks after treatment
E2: Effectiveness 47 days after treatment

EXAMPLE 5

Same combination as that described above. Post-emergence weed control in sugar beet. Volume of mixture: 300 l/ha (France 1990, Marne).

|  | TEST 1 | TEST 2 |
|---|---|---|
| Phenmedipham (l/ha) | 485 | 485 |
| Ethofumesate (l/ha) | 470 | 470 |
| HELIOSOL ® (l/ha) | / | 1 |
| Effectivenesses (E1/E2)* (%/%) |  |  |
| Rape (aftermath) | 3.57/13.51 | 28.57/24.32 |
| Black bindweed | 64.28/61.53 | 71.43/69.23 |
| Poppy | 69.59/73.53 | 86.96/85.29 |

*E1: Effectiveness 2 to 3 weeks after treatment
E2: Effectiveness 47 days after treatment

EXAMPLE 6

Same combination as that described above. Post-emergence weed control in sugar beet. Volume of mixture: 350 l/ha (France 1990, Seine-et-Marne).

|  | TEST 1 | TEST 2 |
|---|---|---|
| Phenmedipham (l/ha) | 485 | 485 |
| Ethofumesate (l/ha) | 470 | 470 |
| HELIOSOL ® (l/ha) | / | 1 |
| Effectivenesses (E1/E2)* (%/%) |  |  |
| Wild chamomile | 0/5.1 | 19.0/36.4 |
| Common fumitory | 84/58 | 88/75 |
| Redshank | 70.6/7.1 | 82.4/71.4 |
| Fat hen | 100/70.8 | 96.9/100 |
| Barnyard grass | 8.3/9.1 | 50/27.3 |

*E1: Effectiveness 15 days after treatment
E2: Effectiveness 30 days after treatment In Examples 4, 5 and 6, HELIOSOL® appears as being selective in sugar beet cultivation.

EXAMPLE 7

HELIOSOL+CELIO combination.

Treatment carried out after the end of winter in post-emergence on soft wheat crops (Soissons variety) infested with foxtail.

The doses applied were as follows, in g/ha or l/ha:
CELIO: 0.4, 0.3 and 0.2
CELIO+HELIOSOL: 0.4+0.75, 0.3+0.75 and 0.2+0.75.

The study was carried out on three 20 m² plots with adjacent control plots.

None of the usual symptoms were observed on the wheat crop at any of the doses (CELIO alone or CELIO+HELIOSOL), which testifies to excellent selectivity.

As regards the effectiveness, the following results were obtained.

CELIO applied alone exhibited an effectiveness with respect to foxtail which was only just acceptable at the dose of 0.4 l/ha in the four tests carried out. The effectiveness falls and becomes unsatisfactory from the dose of 0.3 l/ha.

CELIO applied with 0.75 l/ha of HELIOSOL exhibited effectivenesses which were markedly improved. It is observed that the effectiveness of the CELIO+HELIOSOL mixture, applied at the respective doses of 0.2+0.75 l/ha, makes it possible to obtain an effectiveness with respect to foxtail which is greater than the effectiveness obtained with CELIO applied alone at 0.4 l/ha.

We claim:

1. A dilute selective herbicidal mixture for treating a crop between emergence and flowering of the crop, comprising, per 100 liters of herbicidal mixture, from 0.25 to 1 liter of a formulation comprising from 95% to 60% by weight of a pine oil and from 5 to 40% by weight of a surface-active agent and a selective herbicidal agent.

2. The herbicidal mixture according to claim 1, wherein the formulation comprises 20 to 30% by weight of the surface active agent.

3. The herbicidal mixture according to claim 1, wherein the herbicidal agent is selected from aryloxyphenoxypropionate, phenoxynicotinanilide, benzonitrile, carbamate, benzofuran derivatives, pyridyl phenyl ethers, and mixtures thereof.

4. The herbicidal mixture according to claim 1, wherein the herbicidal agent is selected from fenoxaprop-p-ethyl, diflutenican, ioxynil, bromoxynil and mixtures thereof, phenmedipham, ethofumesate and mixtures thereof; and clodinafop-propargyl+chloquintocetmexyl.

5. A dilute selective herbicidal mixture for treating a crop between emergence and flowering of the crop, comprising, per 100 liters of herbicidal mixture, from 0.25 to 1 liter of a formulation comprising from 95% to 60% by weight of a terpene hydrocarbon or terpene hydrocarbon derivative from 5 to 40% by weight of a surface-active agent, and a selective herbicidal agent.

6. The herbicidal mixture according to claim 5, wherein the formulation comprises 20% to 30% by weight of the surface active agent.

7. The herbicidal mixture according to claim 5, wherein the herbicidal agent is selected from aryloxyphenoxypropionate, phenoxynicotinanilide, benzonitrile, carbamate, benzofuran derivatives, pyridyl phenyl ethers, and mixtures thereof.

8. The herbicidal mixture according to claim 5, wherein the herbicidal agent is selected from fenoxaprop-p-ethyl, diflutenican, ioxynil, bromoxynil and mixtures thereof, phenmedipham, ethofumesate and mixtures thereof; and clodinafop-propargyl+chloquintocetmexyl.

9. The herbicidal mixture according to claim 5, wherein the formulation comprises, as the terpene hydrocarbon or terpene hydrocarbon derivative, 80 to 90% by weight of at least one terpene alcohol and 10 to 20% by weight of at least one terpene hydrocarbon.

10. The herbicidal mixture according to claim 5, wherein the formulation comprises, as the terpene hydrocarbon or terpene hydrocarbon derivative, at least 50% by weight of a terpene alcohol and up to 50% by weight of a terpene hydrocarbon.

11. A method for increasing the efficacy of a selective herbicidal composition for a crop, comprising the steps of:
preparing a formulation comprising an effective amount of a selective herbicidal agent, an effective amount of an emulsifier, and as an efficiency enhancer, a co-formulant which is a combination of at least 50% by weight of a terpene alcohol and up to 50% by weight of a terpene hydrocarbon;

diluting the said formulation to form a diluted herbicidal composition comprising an effective amount of the selective herbicidal agent; and applying the said diluted formulation to the crop between emergence and flowering of the said crop.

12. The method according to claim 11, in which the herbicidal agent is selected from the group consisting of aryloxyphenoxypropionate, phenoxynicotinanilide, benzonitrile, carbamate, benzofuran derivatives, pyridyl phenyl ethers, and mixtures thereof.

13. The method according to claim 11, in which the herbicidal agent is selected from:

(i) fenoxaprop-p-ethyl;

(ii) diflutenican, ioxynil, bromoxynil and mixtures thereof;

(iii) phenmedipham, ethofumesate and mixtures thereof; and (iv) clodinafop-propargyl+chloquintocetmexyl.

14. A method for increasing the efficacy of a selective herbicidal composition for a crop, comprising the steps of:

preparing a formulation comprising an effective amount of a selective herbicidal agent, an effective amount of an emulsifier, and as a co-formulant, a combination of 80 to 90% by weight of at least one terpene alcohol and from 10 to 20% by weight of at least one terpene hydrocarbon;

diluting the said formulation to form a diluted herbicidal composition comprising an effective amount of the selective herbicidal agent; and applying the said diluted formulation to the crop between emergence and flowering of the said crop.

15. A method for increasing the efficacy of a selective herbicidal composition for a crop, comprising the steps of:

preparing a formulation comprising an effective amount of a selective herbicidal agent, an effective amount of an emulsifier, and a co-formulant consisting of pine oil;

diluting the said formulation to form a diluted herbicidal composition comprising an effective amount of the selective herbicidal agent; and applying the said diluted formulation to the crop between emergence and flowering of the said crop.

16. A method for increasing the efficacy of a selective herbicidal mixture for a crop, comprising the steps of:

preparing a diluted herbicidal mixture of a selective herbicidal agent;

adding to said herbicidal mixture from 0.25 liter to 1 liter per 100 liters of an adjuvant comprising a combination of (1) at least 50% by weight of at least one terpene alcohol and up to 50% by weight of at least one terpene hydrocarbon, and (2) a surface active agent; and applying the mixture thus obtained to the crop between emergence and flowering of the said crop.

17. The method according to claim 16 wherein said adjuvant comprises from 5 to 40% by weight of said surface active agent.

18. The method according to claim 16 wherein said adjuvant comprises from 20 to 30% by weight of said surface active agent.

19. The method according to claim 16 wherein said surface-active agent is an alkali sulphate.

20. The method according to claim 16, wherein said herbicidal agent is selected from the group consisting of aryloxyphenoxypropionate, phenoxynicotinanilide, benzonitrile, carbamate, benzofuran derivatives, pyridyl phenyl ethers and mixtures thereof.

21. The method according to claim 16, in which the herbicidal agent is selected from:

(v) fenoxaprop-p-ethyl;

(vi) diflufenican, ioxynil, bromoxynil and mixtures thereof;

(vii) phenmedipham, ethofumesate and mixtures thereof; and (viii) clodinafop-propargyl+chloquintocetmexyl.

22. A method for increasing the efficacy of a selective herbicidal composition for a crop, comprising the steps of:

preparing a diluted herbicidal mixture of a selective herbicidal agent;

adding to said herbicidal mixture from 0.25 liter to 1 liter per 100 liters of an adjuvant comprising a combination of (1) 80 to 90% by weight of at least one terpene alcohol and from 10 to 20% by weight of at least one terpene hydrocarbon, and (2) a surface active agent; and applying the mixture thus obtained to the crop emergence and flowering of the said crop.

23. A method for increasing the efficacy of a selective herbicidal composition for a crop, comprising the steps of:

preparing a diluted herbicidal mixture of a selective herbicidal agent;

adding to said herbicidal mixture from 0.25 liter to 1 liter per 100 liters of an adjuvant consisting of (1) pine oil and (2) a surface active agent; and applying the mixture thus obtained to the crop between emergence and flowering of the said crop.

* * * * *